US008244332B2

(12) United States Patent
Azar et al.

(10) Patent No.: US 8,244,332 B2
(45) Date of Patent: Aug. 14, 2012

(54) THREE-DIMENSIONAL BREAST ANATOMY IMAGING SYSTEM

(75) Inventors: Fred S. Azar, Princeton, NJ (US); Ali Khamene, Princeton, NJ (US); Frank Sauer, Princeton, NJ (US); Bruce Tromberg, Irvine, CA (US); Albert Cerussi, Lake Forest, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 298 days.

(21) Appl. No.: 11/292,338

(22) Filed: Dec. 1, 2005

(65) Prior Publication Data

US 2007/0219450 A1 Sep. 20, 2007

Related U.S. Application Data

(60) Provisional application No. 60/638,231, filed on Dec. 22, 2004.

(51) Int. Cl.
*A61B 6/00* (2006.01)
(52) U.S. Cl. .......................... 600/476; 600/310; 600/473
(58) Field of Classification Search .......................... None
See application file for complete search history.

(56) References Cited

U.S. PATENT DOCUMENTS

| | | | | |
|---|---|---|---|---|
| 4,281,645 A | * | 8/1981 | Jobsis | 600/324 |
| 4,455,609 A | * | 6/1984 | Inamura et al. | 250/370.07 |
| 5,474,073 A | * | 12/1995 | Schwartz et al. | 600/456 |
| 5,831,719 A | * | 11/1998 | Berg et al. | 356/5.13 |
| 5,834,759 A | * | 11/1998 | Glossop | 250/203.1 |
| 5,935,061 A | * | 8/1999 | Acker et al. | 600/304 |
| 6,006,126 A | * | 12/1999 | Cosman | 600/426 |
| 6,058,324 A | * | 5/2000 | Chance | 600/473 |
| 6,195,580 B1 | * | 2/2001 | Grable | 600/473 |
| 6,296,613 B1 | | 10/2001 | Emmenegger et al. | |
| 6,411,838 B1 | * | 6/2002 | Nordstrom et al. | 600/476 |
| 2003/0125623 A1 | * | 7/2003 | Kelly et al. | 600/437 |
| 2003/0184285 A1 | * | 10/2003 | Anderson et al. | 324/207.17 |
| 2004/0015075 A1 | * | 1/2004 | Kimchy et al. | 600/424 |

FOREIGN PATENT DOCUMENTS

WO 92/07233 4/1992

OTHER PUBLICATIONS

Michael Kaschael et al "Applied Optics, vol. 37, No. 10/ Apr. 1, 1998".*
Michael Kaschke et al, "Assessment of the size, position, and optical properties of breat tumors in vivo by noninvasive optical methods".*

* cited by examiner

*Primary Examiner* — Tse Chen
*Assistant Examiner* — Joel F Brutus (57) ABSTRACT

A diffuse optical spectroscopy system comprises a laser breast scanner, a handheld probe connected to the laser breast scanner for scanning a breast, and a tracking device coupled to the handheld probe, wherein the tracking device determines locations of the handheld probe relative to the breast. The tracking device comprises a magnetic tracking device, an optical tracking device or a laser tracking device.

9 Claims, 7 Drawing Sheets

THREE-DIMENSIONAL BREAST ANATOMY IMAGING SYSTEM

CROSS-REFERENCE TO RELATED APPLICATION

This application claims priority to U.S. Provisional Application No. 60/638,231, which was filed on Dec. 22, 2004, and which is incorporated herein by reference in its entirety.

BACKGROUND OF THE INVENTION

1. Technical Field

The present disclosure relates to a breast anatomy imaging system, and more particularly to a breast anatomy imaging system using a handheld optical imaging device combined with a position tracking system.

2. Discussion of Related Art

Presurgical chemotherapy is a treatment commonly used for locally advanced breast cancer. The patient's response to the presurgical chemotherapy is monitored to improve survival and reduce morbidity. A noninvasive, near-infrared technology based on diffuse optical spectroscopy (DOS) has been developed to quantitatively monitor tumor response to the presurgical chemotherapy. The quantitative, near-infrared diffuse optical spectroscopy is capable of distinguishing between tumor and surrounding breast tissues. Thus, diffuse optical spectroscopy is used to monitor tumor response in a patient with locally advanced cancer throughout the course of the therapy.

Diffuse optical spectroscopy uses near-infrared (NIR) light at a specific laser diode wavelength and a broadband steady-state (SS) measurement to quantitatively measure optical properties in tissues. Optical properties such as absorption and scattering parameters derived from the diffuse optical spectroscopy measurement have been used to determine, for example, tissue hemoglobin, oxygen saturation, water content, fat content and cellular structure.

Portable and noninvasive optical probes are used in connection with the diffuse optical spectroscopy. However, a limitation of conventional technologies using the optical probes is the inability to accurately track the position of the optical probe as measurements are recorded. In particular, consistently returning to the same location on the tumor from treatment to treatment is important because variations in contact positions may cause variations in measured optical properties. A pen-marked predefined grid can be used to better locate contact positions.

SUMMARY OF THE INVENTION

According to embodiments of the present invention, the same Region of Interest (ROI) in an organ such as a breast can be measured with each visit, thereby increasing measurement sensitivity by minimizing uncertainties involved with optical handheld probe position placement. Further, by tracking the rotational coordinates of the optical handheld probe on the surface of the breast, the orientation and coupling of the optical handheld probe can be consistent with each measurement and over the range of longitudinal measurements.

According to an aspect of the present invention, an optical handheld probe includes at least a two-dimensional tracking device, which allows measurement over any location on the breast with about 1 mm system accuracy.

According to an embodiment of the present invention, a diffuse optical spectroscopy system comprises a laser breast scanner, a handheld probe connected to the laser breast scanner for scanning a breast, and a tracking device coupled to the handheld probe, wherein the tracking device determines locations of the handheld probe relative to the breast.

The diffuse optical spectroscopy system may further comprise a processor for processing optical data received from the handheld probe and position data received from the tracking device, and a display device for displaying the processed optical data and position data in at least two-dimensional environment. The optical data includes at least one of volume fractions of water, lipid, deoxygenated hemoglobin or oxygenated hemoglobin.

The tracking device according to an embodiment of the present invention may be a magnetic tracking device, an optical tracking device or a laser tracking device. The magnetic tracking device may include a sensor tip and a magnetic tracking base for generating a magnetic field, and a movement of the sensor tip in the magnetic field is sensed by the processor to determine the locations of the handheld probe relative to the breast. The optical tracking device may include an optical marker frame, a marker cluster and a camera, and a movement of the handheld probe including the marker cluster with respect to the position of the optical marker frame can be detected when the handheld probe is positioned in a line of sight of the camera.

The laser breast scanner generates laser beams for imaging the breast. The locations of the handheld probe can be measured continuously. The display device may display a color-coded surface comprising volumetric elements with a volume equal to an average sampled volume in each measurement. The surface can be visually unfolded to obtain a flat display of information spanning an entire measured area. A position, size, and functional or physiological properties of tumor below a surface of the breast can be determined using the optical data and the position data. The functional or physiological properties may include at least one of water, lipid, deoxygenated hemoglobin or oxygenated hemoglobin fractions.

According to another embodiment of the present invention, a diffuse optical spectroscopy system comprises a handheld probe and a tracking device in a first housing, wherein the first housing is sized to be one of handheld and carried on a user, and a processor operable to generate at least two-dimensional representation using data received from the handheld probe and the tracking device.

According to another embodiment of the present invention, a method for scanning tissues using a handheld probe of a diffuse optical spectroscopy system comprises positioning a handheld probe on the tissues, obtaining and processing optical and position data received from the handheld probe, generating at least two-dimensional representation using the optical and position data, and displaying the at least two-dimensional representation.

BRIEF DESCRIPTION OF THE DRAWINGS

Exemplary embodiments of the present invention can be understood in more detail from the following descriptions taken in conjunction with the accompanying drawings, of which.

DETAILED DESCRIPTION OF PREFERRED EMBODIMENTS

Preferred embodiments of the present invention will now be described more fully hereinafter with reference to the accompanying drawings. This invention may, however, be embodied in different forms and should not be construed as limited to the embodiments set forth herein.

An optical imaging device uses light for imaging parts of the human body. Diffuse optical spectroscopy (DOS) is used for, for example, breast cancer detection and monitoring by measuring optical properties such as the absorption and scattering of the tissues. Diffuse optical spectroscopy typically uses red and near-red spectral region because the dominant molecular absorbers within the red or near-red spectral region in tissues include hemoglobin, water and lipids. Unlike mammography or ultrasound method, the DOS is capable of quantifying the optical properties of, for example, the hemoglobin, water and lipids.

Figure 1:
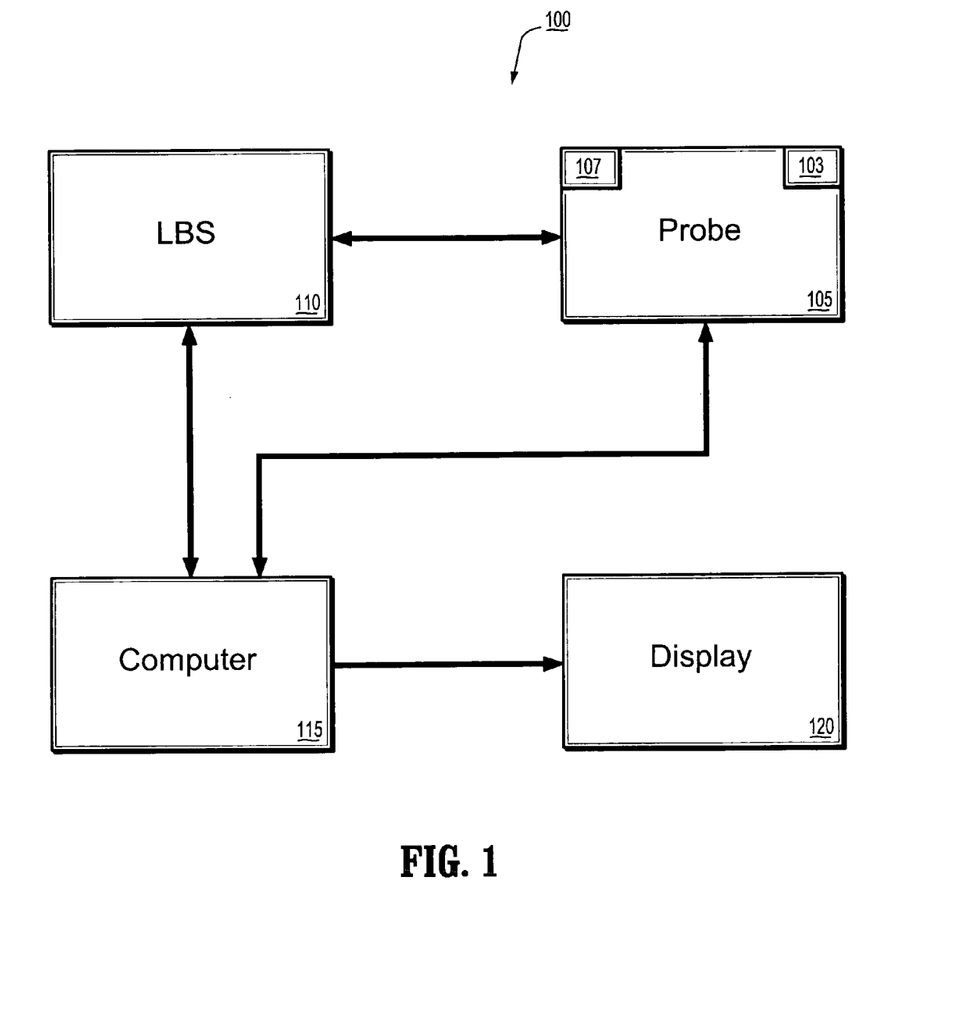
FIG. 1 is a schematic diagram of a diffusion optical spectroscopy (DOS) system according to an embodiment of the present invention.

FIG. 1 shows a schematic diagram of a diffusion optical spectroscopy (DOS) system according to an embodiment of the present invention.

Referring to FIG. 1, the diffuse optical spectroscopy system 100 includes an optical handheld probe 105, a laser breast scanner (LBS) 110, a computer 115, and a display 120. The optical handheld probe 105 includes a tracking device 103 for tracking and positioning the locations of the optical handheld probe 105 and an avalanche photodiode (APD) 107 for detecting the optical properties of the tissues in the breasts. The laser breast scanner 110 connected to the optical handheld probe 105 is used to generate and analyze the laser beam which images the body of the patient. The computer 115 connected to the optical handheld probe 105 and/or the laser breast scanner 110 receives optical property data and position tracking data from the avalanche photodiode 107 and the tracking device 103 of the handheld probe 105, respectively. The optical property data and position tracking data are used to generate two- or three-dimensional representations on the display 120 connected to the computer 115. The connections between the above devices can be either wire or wireless connections.

Figure 2:
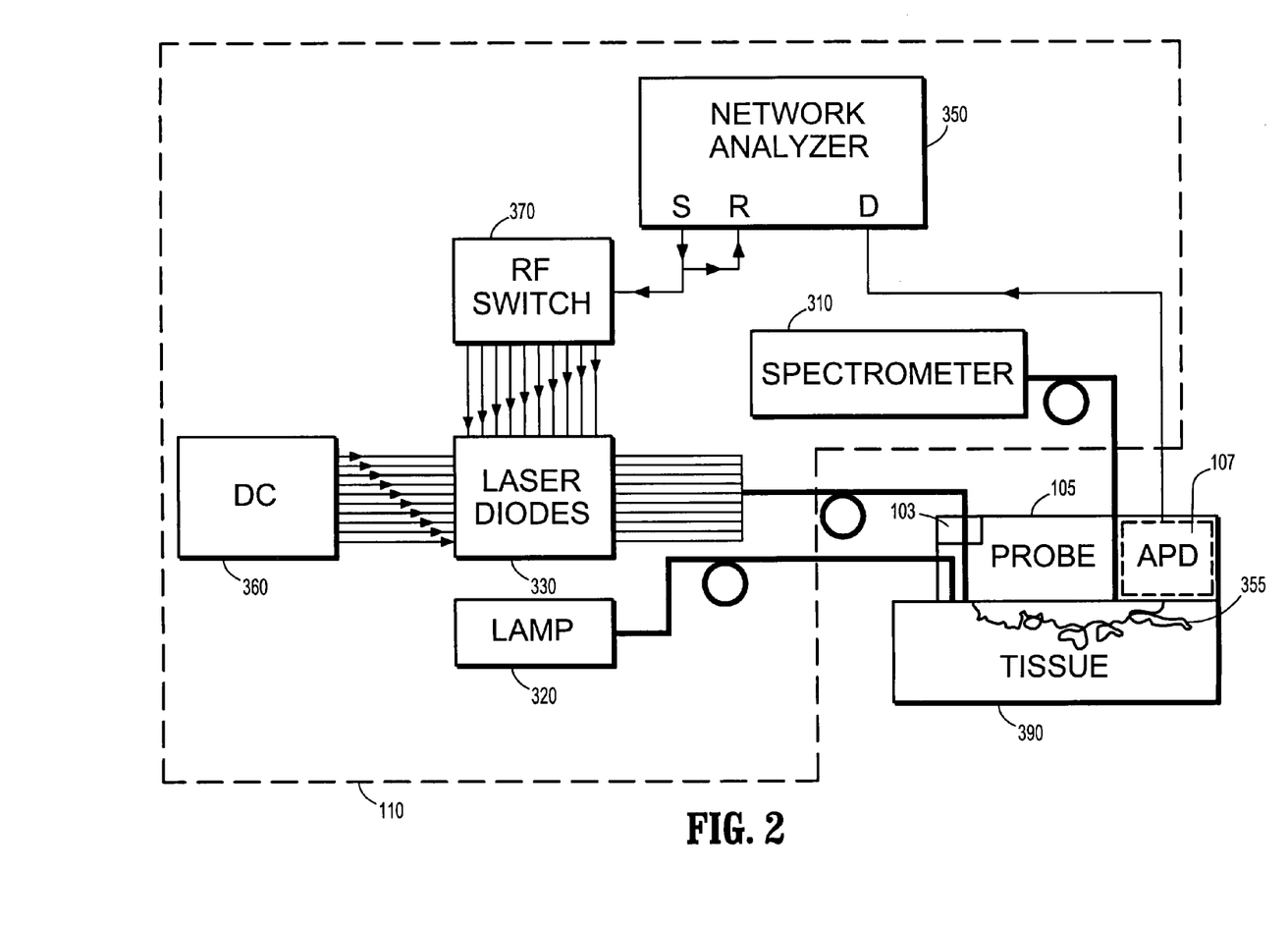
FIG. 2 is a diagram of a laser breast scanner (LBS) combining an optical handheld probe according to an embodiment of the present invention.

FIG. 2 shows a diagram of the laser breast scanner (LBS) 110 combining an optical handheld probe 105 according to an embodiment of the present invention. The laser breast scanner 110 is used to generate and analyze the laser beams which image the breasts of the patient. In an embodiment of the present invention, the laser breast scanner 110 can be, for example, a cart-based system combining the optical handheld probe 105 used for scanning the breasts of the patient. Since the laser breast scanner 110 coupling the optical handheld probe 105 is portable, the laser breast scanner 110 can be used near the bedside of the patient. This easy mobility of the laser breast scanner 110 and the optical handheld probe 105 allows for quantitatively monitoring tumor response, particularly where rapid or frequent measurements are required.

Referring to FIG. 2, the laser breast scanner 110 uses the principles of photon diffusion to quantitatively measure absorption and scattering properties of tissues in the near-infrared spectral region, which is about 650 nm to about 1000 nm. In an embodiment of the present invention, the laser breast scanner 110 includes steady-state (SS) spectroscopy system and frequency-domain (FD) system. The steady-state spectroscopy system comprises a lamp 320 as a high-intensity white-light source and spectrometer 310. The frequency-domain system comprises about 7 to about 10 laser diodes 330 that are intensity modulated using a network analyzer 350. The combination of frequency-domain system and steady-state spectroscopy system allows for acquisition of broadband near-infrared absorption spectra.

In an embodiment of the present invention, the frequency-domain system uses, for example, ten diode lasers coupled to 40 microns step-index optical fibers (not shown) formed into a single bundle. Laser wavelengths to measure absorption and scattering of the tissues can be, for example, 660 nm, 685 nm, 786 nm, 809 nm, 822 nm, 852 nm, 898 nm, 911 nm, 946 nm and 973 nm. Direct current (DC) 360 is applied sequentially to each diode in laser diodes 330, followed by about 50 MHz to about 1000 MHz radio frequency pulse through a RF switch 370 from the network analyzer 350. This produces amplitude-modulated light that, when launched into the tissues 390, propagates with a frequency-dependent phase velocity as diffuse photon density waves. Changes in photon density wave phase and amplitude are detected by the avalanche photodiode 107 in the optical handheld probe 105.

The laser breast scanner 110 can record complete absorption and scattering coefficient spectra from about 600 nm to about 1000 nm. Measurements are recorded in reflectance (i.e., backscattering) geometry 355. The lamp 320 can be, for example, a high-intensity tungsten-halogen for irradiating the tissues 390. Diffuse reflectance is measured using a fiber coupled to the spectrometer 310. A complete spectral measurement using the optical handheld probe 105 in the laser breast scanner 110 comprising steady-state system and frequency-domain system requires about 30 to about 45 seconds.

Figure 3:
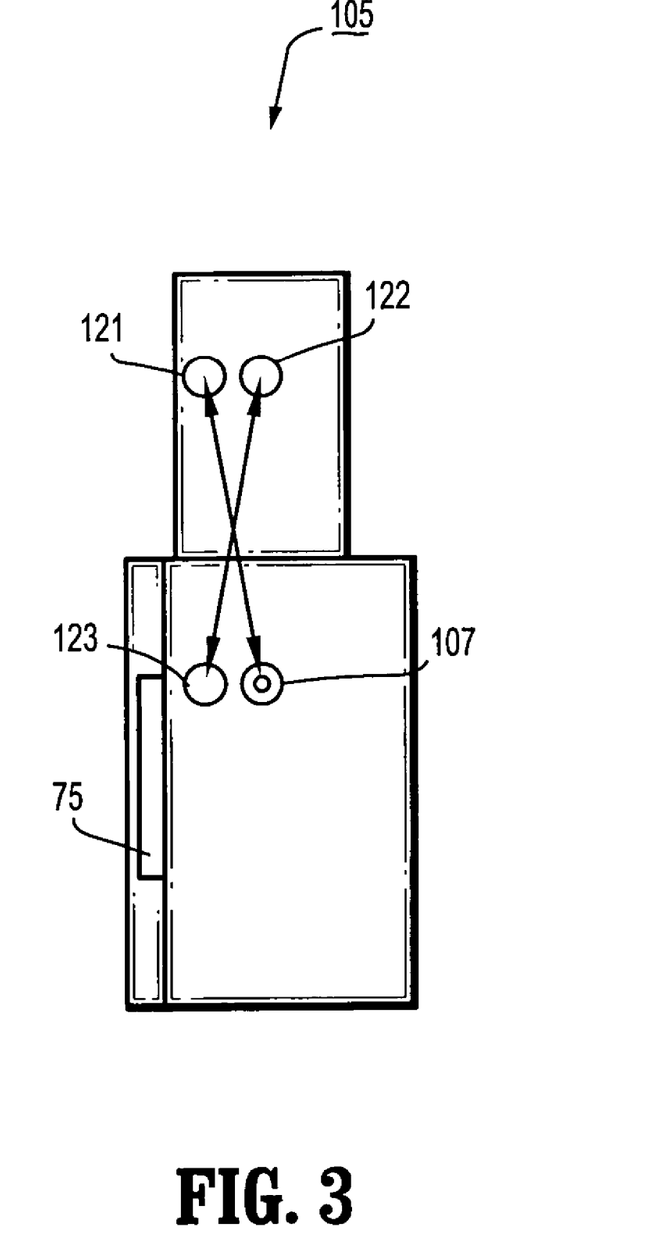
FIG. 3 is a sectional view of the optical handheld probe according to an embodiment of the present invention.

FIG. 3 shows a sectional view of the optical handheld probe 105 according to an embodiment of the present invention. According to an embodiment of the present invention, the optical handheld probe 105 connected to the laser breast scanner 110 is used to detect the tissues of the breast. For example, the optical handheld probe 105 is placed onto a region of interest (ROI), i.e., the surface of the breast. Since the optical handheld probe 105 is small and light enough to be held using one hand, the optical handheld probe 105 can be manipulated spatially without causing discomfort or tiredness on the hand and arm for long periods of time such as about 10 minutes to about 30 minutes.

Referring to FIG. 3, three optical fibers, including steady-state (SS) source fiber 122, frequency-domain (FD) source fiber 121 and steady-state (SS) detector fiber 123, and the avalanche photodiode (APD) 107 are disposed in the optical handheld probe 105. In this embodiment, the steady-state and the frequency-domain measurement paths cross one another, allowing the steady-state and frequency-domain sources to probe approximately the same volume of tissues. A temperature control element 75 and a fan (not shown) stabilize the temperature. Modulated light from the laser diodes 330 is detected by the avalanche photodiode 107 disposed in the optical handheld probe 105. Light of the lamp 320 is detected by another fiber that is directed to the spectrometer 310.

The position tracking system for the optical handheld probe 105 according to an embodiment of the present invention includes, for example, a magnetic tracking system, an optical tracking system, and a laser tracking system.

Figure 4:
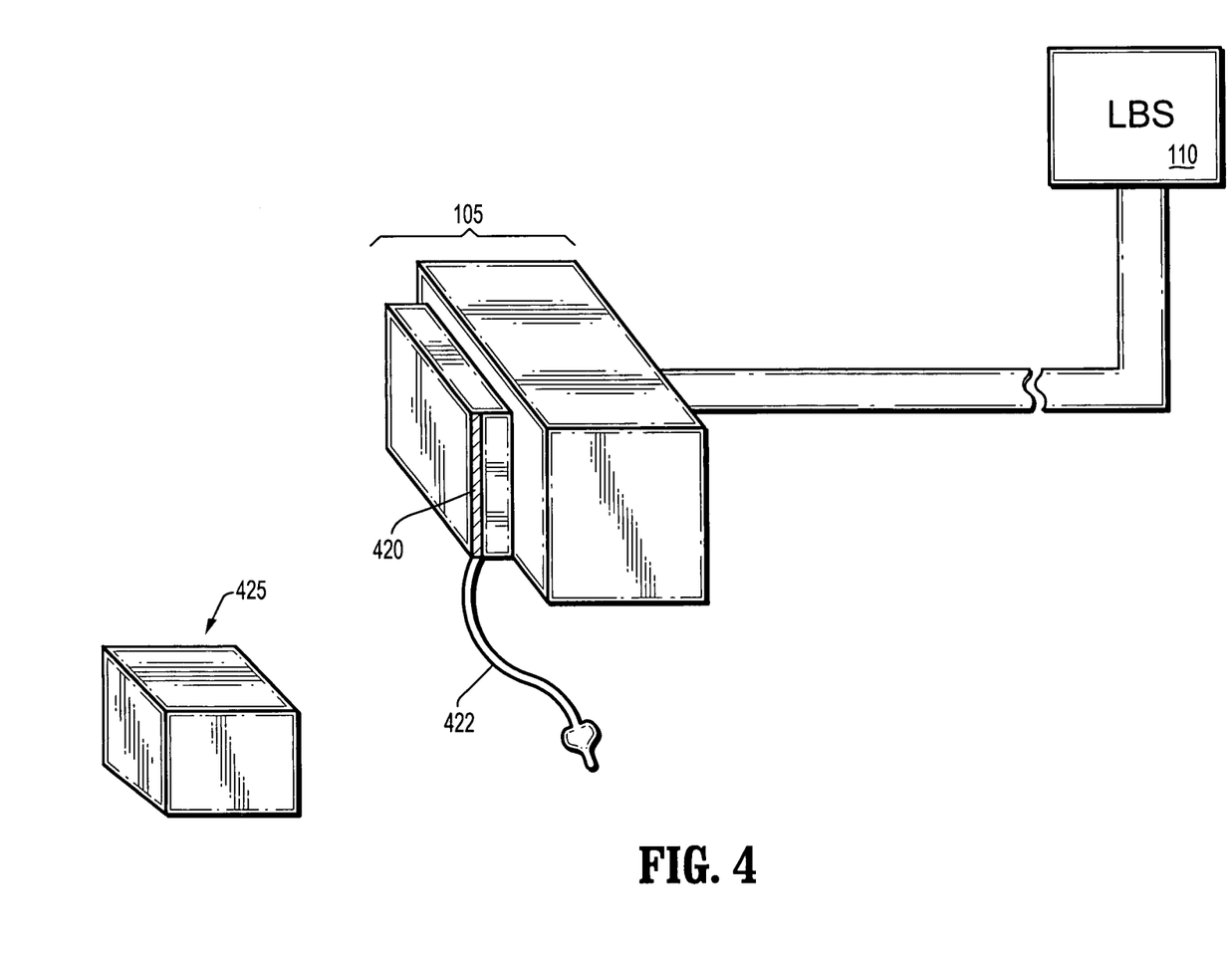
FIG. 4 shows an optical handheld probe using a magnetic tracking system for tracking the positions of the optical handheld probe according to an embodiment of the present invention.

FIG. 4 shows an optical handheld probe 105 using the magnetic tracking system for tracking the positions of the optical handheld probe 105 according to an embodiment of the present invention. The magnetic tracking system includes a sensor tip 420 and a magnetic base 425.

Referring to FIG. 4, the sensor tip 420 is attached to a side of the optical handheld probe 105. However, the sensor tip 420 can be attached to any part of the optical handheld probe 105. The sensor tip 420 can be connected to an electronic unit on a printed circuit board (PCB) configured in the computer 115 using either a wire 422 or a wireless to provide position data of the optical handheld probe 105 to the computer 115. The magnetic base 425 generates a magnetic field in and around the breast of the patient. The magnetic base 425 can be located, for example, near patient's bed. However, the locations of the magnetic base 425 can vary based on strength and shapes of the magnetic base 425. In an embodiment of the present invention, the magnetic tracking base comprises a cube having about a 15 cm side. Alternatively, a flat sheet shaped tracking base can be used.

According to an embodiment of the present invention, the sensor tip 420 attached to the optical handheld probe 105 is located inside the magnetic field. The movement of the sensor tip 420 in the magnetic field is sensed by the computer 115. Thus, the positions of the optical handheld probe 105 can be determined by the computer 115, for example, in three-dimensional spaces. The magnetic tracking system according to an embodiment of the present invention can be either two- or three-dimensional tracking system. Six degrees of freedom for specifying a motion of the optical handheld probe 105 can be achieved using the three-dimensional tracking system. The magnetic tracking system can be used to continuously measure positions and orientations of the optical handheld probe 105 during the presurgical chemotherapy. For example, stop and go or continuous scanning positions are available for the optical handheld probe 105 according to an embodiment of the present invention. MicroBIRD™ magnetic tracker is an exemplary magnetic tracking system. As one of ordinary skill in the art would appreciate, other magnetic tracking systems can also be used.

Figure 5A:
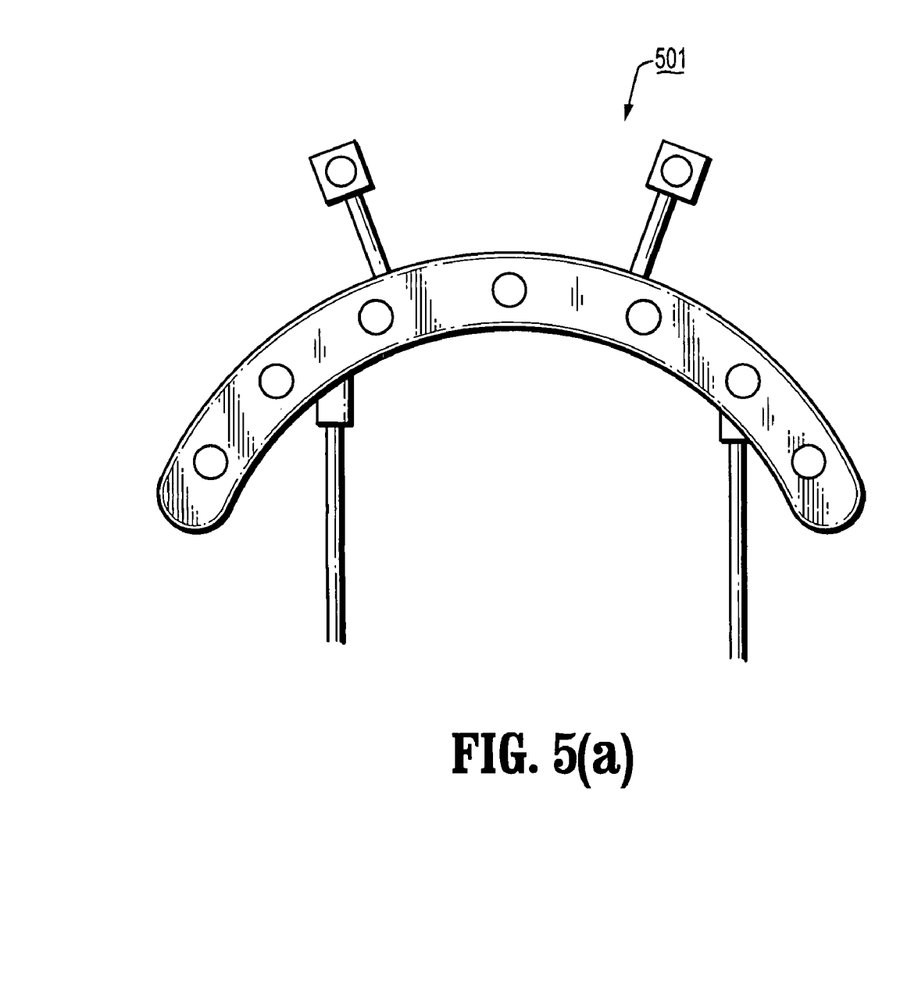
FIG. 5(a) is an optical marker frame for the optical tracking system according to an embodiment of the present invention.
Figure 5B:
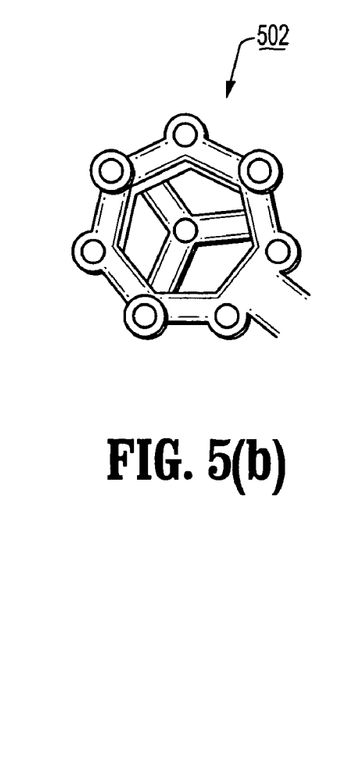
FIG. 5(b) is a marker cluster for the optical tracking system according to an embodiment of the present invention.

In another embodiment of the present invention, an optical tracking system can be used to determine the positions of the optical handheld probe 105. The optical tracking system includes, for example, a camera, an optical marker frame and a marker cluster. FIG. 5(a) shows an optical marker frame 501 for the optical tracking system according to an embodiment of the present invention. FIG. 5(b) shows a marker cluster 502 for the optical tracking system disposed in the optical handheld probe 105 according to an embodiment of the present invention.

The camera (not shown) can be positioned anywhere in the room where the patient is treated to have a direct access to the optical marker frame 501. The camera can detect the position of the marker cluster 502 in the optical handheld probe 105, thereby determining the locations of the optical handheld probe 105. For example, the optical marker frame 501 is attached to the bed of patient and the camera is attached to the ceiling of the room. A distance from the camera to the optical marker frame 501 is automatically measured. Thus, when the optical handheld probe 105 including the marker cluster 502 is positioned in the line of sight of the camera, the movement of the optical handheld probe 105 with respect to the position of the optical marker frame 501 is detected. To obtain an accurate measurement in the optical tracking system, it is preferred that the optical tracking system has an unobstructed line-of-sight between the camera and the optical marker frame 501. According to an embodiment of the present invention, multi-camera systems (not shown) find two-dimensional marker locations in the cameras' images and determine their three-dimensional location by triangulation. A stereo camera system can also be used. As one of ordinary skill in the art would appreciate, other optical tracking systems can also be used.

According to another exemplary embodiment of the present invention, a laser-based tracking system can also be used. Exemplary laser-based tracking systems are described in: 1) Smart Laser-Scanner for 3D Human-Machine Interface by A. Cassinelli, S. Perrin and M. Ishikawa, ACM SIGCHI 2005 (CHI '05) International Conference on Human Factors in Computing Systems, Portland, Oreg., USA Apr. 2-07, 2005, pp. 1138-1139 (2005); 2) Markerless Laser-based Tracking for Real-Time 3D Gesture Acquisition by A. Cassinelli, S. Perrin and M. Ishikawa, ACM SIGGRAPH 2004, Los Angeles; 3) Gesture Recognition Using Laser-based Tracking System by S. Perrin, A. Cassinelli and M. Ishikawa, 6th International Conference on Automatic Face and Gesture Recognition 2004 (FG 2004), Seoul, Korea, 17-19 May 2004; and 4) Laser-Based Finger Tracking System Suitable for MOEMS Integration by S. Perrin, A. Cassinelli and M. Ishikawa, Image and Vision Computing, New Zealand (IVCNZ 2003), Massey Univ., 26-28 Nov. 2003, pp. 131-136, (2003). The entire contents of the four references are incorporated herein by reference.

The computer 115 according to embodiments of the present invention creates an interface simultaneously acquiring all spatial and optical measurements. For example, the computer 115 can generate a three-dimensional environment capable of displaying and manipulating the acquired data regarding, for example, water fraction, lipid fraction, deoxygenated hemoglobin and oxygenated hemoglobin in a clinically useful form. The clinically useful form includes, for example, a three-dimensional cloud of points, a color-coded surface based on DOS measurements, a visual unfolding of the surface to obtain a flat display of information spanning the entire measured area, and time-varying two- or three-dimensional display showing evolution of these quantities over time after serial data registration. Further, a three-dimensional breast anatomical map can be generated. In another embodiment of the present invention, the computer 115 reconstructs the position and size of tumor below the breast surface using the measured information. The computer 115 also assesses reproducibility of the measurement technique by tracking the specific measurement sites on the patient.

Since the region of interest (ROI) of the breast of patient is not in the same position with respect to, for example, the magnetic coordinate system when the patient returns, the computer 115 can implement a serial image registration algorithm capable of registering patient breast data based on three-dimensional topology of the breast. The registration can be achieved based on measuring the coordinates of some body landmarks. Alternatively, the registration can be achieved based on acquiring many surface points with any tracking system.

According to an embodiment of the present invention, the display 120 connected to the computer 115 displays the measured quantities regarding, for example, water fraction, lipid fraction, deoxygenated hemoglobin, and oxygenated hemoglobin in a three-dimensional environment by creating a color-coded surface. The color-coded surface can comprise volumetric elements with a volume equal to an average sampled volume in each measurement.

Figure 6:
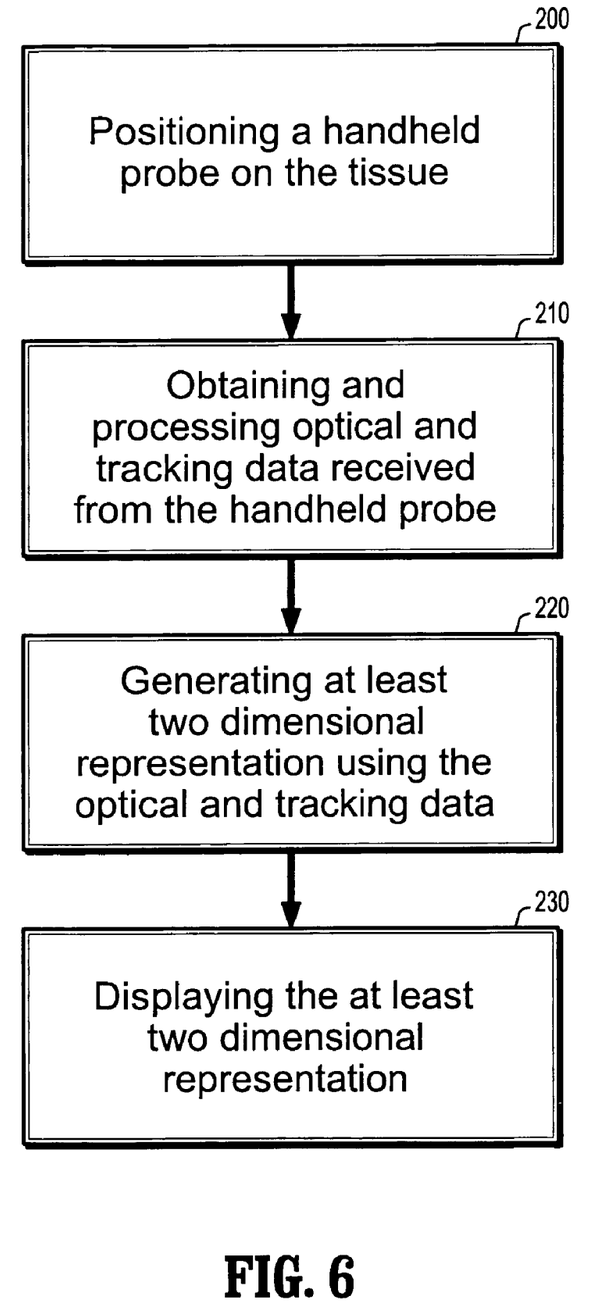
FIG. 6 is a flowchart describing a method for scanning tissues using an optical handheld probe of a diffuse optical spectroscopy system according to an embodiment of the present invention.

FIG. 6 is s a flowchart describing a method for scanning tissues using an optical handheld probe of the diffuse optical spectroscopy (DOS) according to an embodiment of the present invention. Referring to FIG. 6, in step 200, the optical handheld probe 105 including a tracking system is positioned on the tissues of a patient. The tracking system includes a magnetic, an optical and a laser tracking system. In step 210, optical and position data are transferred to the computer 115 from the optical handheld probe 105 to be processed. In step 220, two- or three-dimensional representations can be generated by the computer 115 using the optical and tracking data received from the optical handheld probe 105. In step 230, the two- or three-dimensional representation is displayed on the display 120.

In another exemplary embodiment of the present invention, the measured optical and position data from the DOS can be used in combination with data obtained from a process using an imaging utility such as, for example, a magnetic resonance imaging (MRI). For example, an MRI process is performed to image internal structures of the breasts, and the DOS using the optical handheld probe 105 is performed on the breasts. Then, the information such as an image of the breast structures from the MRI process can be superimposed, for example, on the two-dimensional surface of the breasts displayed on the display 120.

Figure 7:
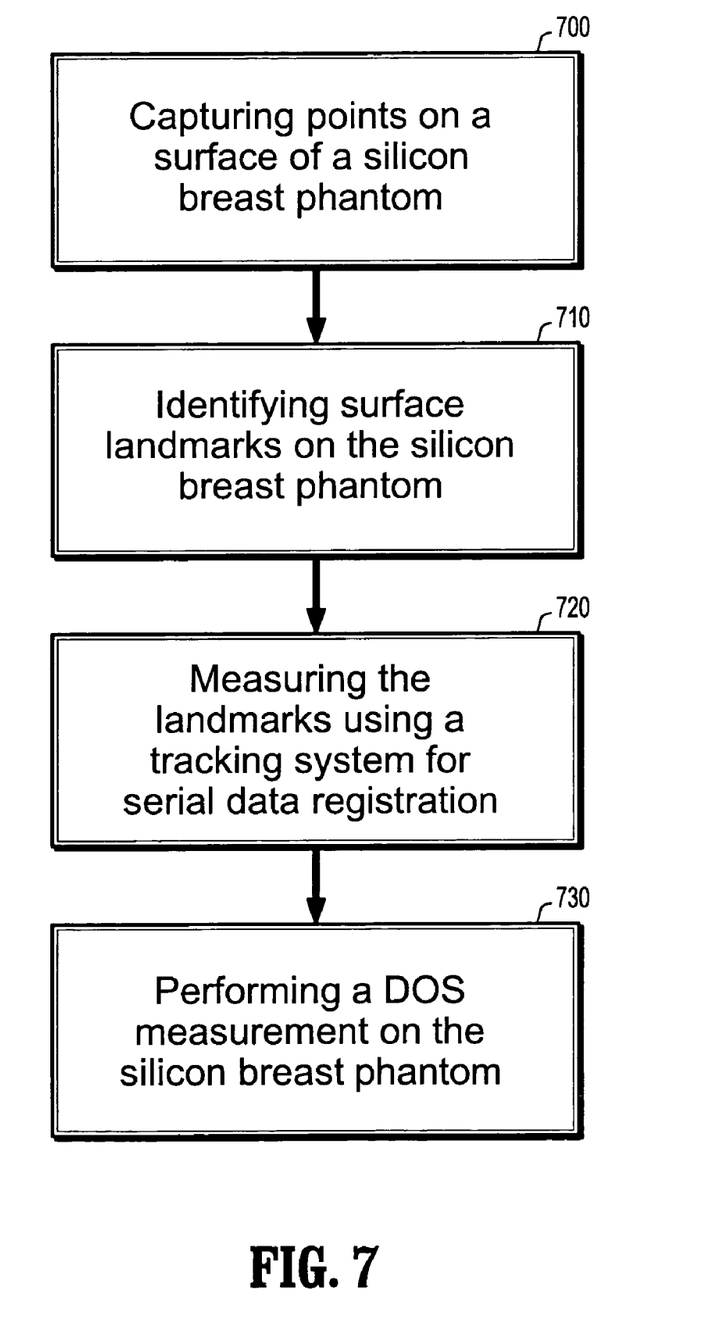
FIG. 7 is a flowchart describing a method for testing the reliability of a tracking system by performing repeated measurements on a silicone breast phantom according to an embodiment of the present invention.

FIG. 7 is a flowchart describing a method for testing the reliability of the tracking systems by performing repeated measurements on a silicon breast phantom according to an embodiment of the present invention. The silicon breast phantom includes an inclusion. Reproducibility can be tested both on a daily basis and on a weekly basis to simulate various longitudinal measurements. Referring to FIG. 7, in step 700, the tracking system is used to capture enough points on the phantom surface and create a surface model. In step 710, known surface landmarks on the phantom are identified. In step 720, the landmarks using the tracking system are measured for serial data registration in longitudinal studies. In step 730, the DOS measurements on the phantom are performed.

Although preferred embodiments have been described herein with reference to the accompanying drawings, it is to be understood that the present invention is not limited to these precise embodiments, but various changes and modifications can be made by one skilled in the art without departing from the spirit and scope of the present invention. All such changes and modifications are intended to be included within the scope of the invention as defined by the appended claims.

What is claimed is:

1. A diffuse optical spectroscopy system, comprising:
a tracking device including a first member and a second member;
a handheld probe including an avalanche photodiode (APD) for detecting optical properties of tissues in a region of interest of a patient and the first member of the tracking device communicating with the second member for determining locations of the handheld probe relative to the region of interest; and
a processor operable to
generate at least a two-dimensional representation using data of the optical properties and data of the determined locations of the handheld probe relative to the region of interest, wherein the data of the optical properties includes at least two of volume fractions of water, lipid, deoxygenated hemoglobin and oxygenated hemoglobin,
generate a color-coded surface in the two-dimensional representation, wherein the color-coded surface displays measured quantities corresponding to the at least two volume fractions and the measured quantities are displayed using different colors,
register serial images of the optical properties in the region of interest based on the determined locations, and
reconstruct a position and a size of a tumor below a surface in the region of interest of a later serial image using the registration of the serial images based on the determined locations.

2. The diffuse optical spectroscopy system of claim 1, wherein the tracking device is a magnetic tracking device, an optical tracking device or a laser tracking device.

3. The diffuse optical spectroscopy system of claim 2, wherein the first member is a sensor tip and the second member is a magnetic tracking base for generating a magnetic field, and a movement of the sensor tip in the magnetic field is sensed by the processor to determine locations of the handheld probe relative to the region of interest.

4. The diffuse optical spectroscopy system of claim 2, wherein the optical tracking device includes an optical marker frame, a marker cluster and a camera, and a movement of the handheld probe including the marker cluster with respect to the position of the optical marker frame is detected when the handheld probe is positioned in a line of sight of the camera.

5. The diffuse optical spectroscopy system of claim 1, further comprising a display device for displaying the at least two-dimensional representation.

6. The diffuse optical spectroscopy system of claim 1, wherein a volume of the color-coded surface is equal to an average sampled volume in each measured quantity.

7. The diffuse optical spectroscopy system of claim 6, wherein the surface is visually unfolded to obtain a flat display of information spanning an entire measured area.

8. A method for scanning a patient using a handheld probe of a diffuse optical spectroscopy system, the method comprising:
detecting optical properties of tissues in a region of interest of the patient;
determining locations of the handheld probe relative to the region of interest;
generating at least a two-dimensional representation using data of the optical properties and data of the determined locations of the handheld probe relative to the region of interest, wherein the data of the optical properties includes at least two of volume fractions of water, lipid, deoxygenated hemoglobin and oxygenated hemoglobin;
generating a color-coded surface in the two-dimensional representation, wherein the color-coded surface displays measured quantities corresponding to the at least two volume fractions and the measured quantities are displayed using different colors;
registering serial images of the optical properties in the region of interest based on the determined locations;
reconstructing a position and a size of a tumor in the region of interest of a later serial image using the registration of the serial images based on the determined locations; and time-varying the two-dimensional representation using the registered serial images, wherein the time-varied representation shows a change of the measured quantities over time.

9. The method of claim 8, further comprising:
performing a magnetic resonance imaging process; and
superimposing data obtained from the magnetic resonance imaging process on the at least two-dimensional representation.

* * * * *